(12) United States Patent
Yee et al.

(10) Patent No.: US 7,267,831 B2
(45) Date of Patent: Sep. 11, 2007

(54) PROCESSED CHEESE WITH IMPROVED FIRMNESS USING CROSS-LINKING ENZYMES

(75) Inventors: Jeng-Jung Yee, Green Bay, WI (US); Charles C. Hunt, DePere, WI (US)

(73) Assignee: Schreiber Foods, Inc., Greenbay, WI (US)

( * ) Notice: Subject to any disclaimer, the term of this patent is extended or adjusted under 35 U.S.C. 154(b) by 626 days.

(21) Appl. No.: 10/382,227

(22) Filed: Mar. 4, 2003

(65) Prior Publication Data

US 2003/0165594 A1 Sep. 4, 2003

Related U.S. Application Data

(60) Provisional application No. 60/361,828, filed on Mar. 4, 2002.

(51) Int. Cl.
*A23C 9/12* (2006.01)
(52) U.S. Cl. ............ 426/36; 426/34; 426/38; 426/520; 426/582
(58) Field of Classification Search .......... 426/34, 426/36, 38, 40, 520, 580, 582
See application file for complete search history.

(56) References Cited

U.S. PATENT DOCUMENTS

| | | | |
|---|---|---|---|
| 5,156,956 | A | 10/1992 | Motoki et al. |
| 5,356,639 | A | 10/1994 | Jameson et al. |
| 5,681,598 | A | 10/1997 | Kuraishi et al. |
| 5,750,177 | A | 5/1998 | Yee et al. |
| 5,866,180 | A | 2/1999 | Budolfsen et al. |
| 6,093,424 | A | 7/2000 | Han et al. |
| 6,214,404 | B1 | 4/2001 | Han et al. |
| 6,224,914 | B1 | 5/2001 | Han et al. |
| 6,242,036 | B1 | 6/2001 | Han et al. |
| 6,251,445 | B1 | 6/2001 | Han et al. |
| 6,258,390 | B1 | 7/2001 | Budiz |
| 6,270,814 | B1 | 8/2001 | Han et al. |

FOREIGN PATENT DOCUMENTS

| | | |
|---|---|---|
| EP | 1 057 412 A2 | 12/2000 |
| JP | 2594340 B2 | 3/1997 |
| WO | WO93/22930 | 11/1993 |
| WO | WO94/21129 | 9/1994 |
| WO | WO94/21130 | 9/1994 |

OTHER PUBLICATIONS

Fox, Patrick et al., *Fundamentals of Cheese Science*, Aspen Publishers, Inc., copyright 2000, p. 428.
AJINOMOTO brochure Activa TG-TI, undated but printed prior to Dec. 13, 2001, 5 pages.
AJINOMOTO brochure Basic Properties of Transglutaminase, undated but printed prior to Dec. 13, 2001, 7 pages.
AJINOMOTO brochure General Information about Transglutaminase, What is TG?, undated but printed prior to Dec. 13, 2001, 5 pages.

*Primary Examiner*—Leslie Wong
(74) *Attorney, Agent, or Firm*—Steven P. Shurtz; Brinks Hofer Gilson & Lione

(57) ABSTRACT

A method of making a processed cheese with improved firmness comprises mixing a protein cross-linking enzyme and optionally first other ingredients with a cheese material having a pH of less than 5.6, a moisture content of less than 60% and preferably containing one or more coagulating agents, to form a mixture; providing temperature and pH conditions and allowing time for the enzyme to react with protein in the mixture to cross link at least a portion of the protein; and combining one or more emulsifying agents and optionally second other ingredients with the mixture and heating the combination to thereby produce processed cheese from the combined cheese material contain cross-linked proteins, emulsifying agents and optional first and second other ingredients.

39 Claims, No Drawings

PROCESSED CHEESE WITH IMPROVED FIRMNESS USING CROSS-LINKING ENZYMES

REFERENCE TO EARLIER FILED APPLICATION

The present application claims the benefit of the filing date under 35 U.S.C. § 119(e) of Provisional U.S. Patent Application Ser. No. 60/361,828, filed Mar. 4, 2002, which is hereby incorporated by reference in its entirety.

BACKGROUND OF THE INVENTION

The present invention relates to processed cheese and methods of making processed cheese. In particular, the invention relates to the use of a protein cross-linking enzyme during the manufacturing process to produce a processed cheese having an improved firmness.

Processed cheese has become a staple of the food industry. It is also a commodity, meaning that there are many suppliers of processed cheese. As a result, the price charged for processed cheese has a great impact on a supplier's share of the market. Thus processed cheese manufacturers are under constant pressure to reduce their costs. On the other hand, government regulations regarding the ingredients that can be used, and the desire for functional qualities such as taste, firmness, mouth feel and meltability, constrain efforts to reduce costs. In addition to the quality perceived by the consumer, functional qualities are also important in the manufacturing process.

One of the efforts to reduce cost for cheese has been to keep the whey proteins from being lost in the cheese making process. For example, U.S. Pat. No. 5,356,639 discloses a process for making cheese by using ultrafiltration and diafiltration to keep all of the whey proteins in the final cheese. Also, U.S. Pat. No. 5,681,598 discloses the use of transglutaminase to cross-link proteins in milk to increase the yield of the curds from the milk. In addition, whey solids are a common ingredient mixed with cheese to make processed cheese. However, the presence of whey solids in processed cheese has a negative impact on the firmness of the processed cheese. Other ingredients that may he added to processed cheese may also have a negative impact on the firmness or meltability of the processed cheese. Also, many other measures taken to reduce cost often have a negative impact on the firmness of processed cheese.

Transglutaminase has been suggested for use in various food products. Transglutaminase cross-links proteins in meat products to improve the hardness and elasticity of the products, as well as to improve the texture of products containing low meat content. Transglutaminase has also been disclosed for use in dairy products. For example, U.S. Pat. No. 6,224,914 discloses a process for incorporating whey proteins into cheese using transglutaminase, and U.S. Pat. No. 6,242,036 discloses cheese curd made using transglutaminase and a non-rennet protease. U.S. Pat. No. 6,270,814 discloses incorporation of whey into process cheese. However, the common problem with many of these processes is that transglutaminase is currently fairly expensive. Thus, the benefit it provides is not worth its cost. None of the foregoing processes using transglutaminase are believed to be currently used on a commercial basis in the United States.

Another approach for utilizing transglutaminase in processed cheese is disclosed in Japanese Patent Publication No. 2594340. In the disclosed process, cheese and other ingredients are melted, mixed together and cooked to make a processed cheese. The temperature is then reduced and transglutaminase is added and allowed to act on the melted cheese mixture to produce a product with optimal stringiness and high temperature shape retention. One problem with this process is that the processed cheese is stirred at a medium temperature, such as 50° C. (122° F.), for 30 minutes while the transglutaminase reacts. This material then has to be reheated to 85° C. (185° F.) to deactivate the transglutaminase. All of this post-manufacture processing of the processed cheese is impractical in making a commodity processed cheese, which otherwise requires only a very short residence time in the mixing and cooking equipment.

Hence, there is still a need for a process for making processed cheese that has good firmness, but which is commercially practical. Also, a processed cheese that is inexpensive, but still has good firmness and melt properties would be highly desirable.

BRIEF SUMMARY OF THE INVENTION

A process has been invented that allows an efficient use of a protein cross-linking enzyme, such as transglutaminase, in making a processed cheese with improved firmness.

In a first aspect, the invention is a method of making a processed cheese with improved firmness comprising: mixing a protein cross-linking enzyme and optionally first other ingredients with a cheese material having a pH of less than 5.6, a moisture content of less than 60% and preferably containing one or more coagulating agents to form a mixture; providing temperature and pH conditions and allowing time for the enzyme to react with protein in the mixture to cross link at least a portion of the protein; and thereafter combining one or more emulsifying agents and optionally second other ingredients with the mixture and heating the combination to thereby produce processed cheese from the combined cheese material containing cross-linked proteins, emulsifying agents and optional first and second other ingredients.

In a second aspect, the invention is a method of making a processed cheese comprising: producing cheese curds; mixing transglutaminase with the cheese curds; packing the mixture of cheese curds and transglutaminase to form cheese; allowing the cheese to age for a period of at least 24 hours, the transglutaminase reacting with protein in the curds to cross-link the protein while the cheese is aging; and combining the transglutaminase-treated cheese with other processed cheese ingredients and heating and mixing the combination to produce the processed cheese.

In a third aspect, the invention is a method of making processed cheese comprising: ultrafiltering and diafiltering milk to produce a retentate; fermenting the retentate; adding transglutaminase to the retentate; removing water from the fermented retentate; providing temperature and pH conditions and allowing a period of time for the transglutaminase to cross link at least a portion of proteins in the retentate; and combining the fermented dewatered retentate with cross-linked proteins therein with other processed cheese ingredients, and heating and mixing the combination to produce the processed cheese.

In a fourth aspect, the invention is a method of making processed cheese comprising: providing cheese material and other ingredients used to make the processed cheese; mixing transglutaminase with the cheese material and providing temperature and pH conditions and allowing time for the transglutaminase to cross link at least a portion of proteins in the cheese material; and heating and mixing the cheese material, transglutaminase and other processed cheese ingredients to form the processed cheese.

The present invention also encompasses a processed cheese made by any of the foregoing methods, as well as novel intermediate compositions and methods of adding a protein cross-linking enzyme to a cheese material. In this regard, in another aspect the invention is a mixture of a cheese material and a protein cross-linking enzyme comprising: a cheese material selected from the group consisting of comminuted natural cheese, conventional cheese curds and fermented UF retentate, and transglutaminase, wherein the transglutaminase is present at a level of between about 0.2 units and about 10 units of transglutaminase per gram of protein in the mixture.

In yet another aspect, the invention is a process of adding a protein cross-linking enzyme to a cheese material so as to allow the enzyme to cross link protein in the cheese material comprising the steps of: ultrafiltering and diafiltering milk to produce a UF retentate; adding transglutaminase to the retentate at a level of between about 0.2 units and about 10 units of transglutaminase per gram of protein in the UF retentate; and evaporating water from the retentate to produce a UF cheese containing active transglutaminase.

In still yet a further aspect, the invention is a process of adding a protein cross-linking enzyme to a cheese material so as to allow the enzyme to cross link protein in the cheese material comprising the steps of: producing conventional cheese curds; mixing transglutaminase with the cheese curds at a level of between about 0.2 units and about 10 units of transglutaminase per gram of protein in the curds; and packing the mixed curds and transglutaminase into a container.

In addition to increased firmness, there are other advantages of the present invention. Primarily, the cross-linking enzyme is utilized in a composition that has a fairly high solids level. In many of the prior art processes, transglutaminase is used in milk, or other dilute casein sources, or compositions where casein only makes up a small percentage of the composition. As a result, either large quantities of transglutaminase must be used, or long reaction times must be allowed, both of which are not very cost efficient. Further, in the present invention, the cross-linking enzyme is preferably mixed with a cheese material at a stage in the overall processed cheese manufacturing process when the cheese material (such as cheese curds or UF cheese) is normally given time to age. As a result, in preferred embodiments of the invention, the cross-linking reaction can occur over a fairly long period of time without adding to the time required to actually make the processed cheese.

Finally, the preferred embodiments of the invention utilize temperatures normally encountered in processed cheese manufacturing processes to deactivate the cross-linking enzyme, as opposed to additional mixing, holding and deactivation steps after processed cheese is made.

These and other advantages of the invention, as well as the invention itself, will be best understood in light of the following detailed description and examples, which are given by way of explanation and are not to be considered as limiting the invention.

DETAILED DESCRIPTION OF THE INVENTION AND PREFERRED EMBODIMENTS

Definitions

Unless indicated otherwise, percentages given for components in a composition are percentages by weight of the composition. "Conventional cheese" as used herein means a cheese made by the traditional method of coagulating milk, cutting the coagulated milk to form discrete curds, stirring and heating the curd, draining off the whey, and collecting or pressing the curd. Milk from many different mammals is used to make cheese, though cow's milk is the most common milk for cheese used to make processed cheese. Cow's milk contains whey proteins and casein at a weight ratio of about 1:4 whey proteins to casein. The conventional process for making natural cheese recovers the casein from the milk. Whey proteins dissolved in the whey are mostly discharged during the whey drainage step. The ratio of whey proteins to casein is between about 1:150 and about 1:40 for conventional cheese. For example, Cheddar cheese contains about 0.3% whey proteins. The ratio of whey proteins to casein is about 1:100 in typical Cheddar cheese, the most common conventional cheese. Cheddar cheese contains about 23% to about 26% protein by weight. Conventional cheese is often categorized by its age. Within 0 to 24 hours after the whey is drained, the material is often referred to as fresh curd. The curds are pressed and fused together to become cheese. Young cheese is often categorized as cheese that has been aged either 1-7 days, 1-2 weeks or 2 weeks to 1 month. Medium cheese is often categorized as aged 1-3 months or 3-6 months. Aged cheese is usually older than 6 months. "American-type cheeses" as used herein means the group of conventional cheeses including Cheddar, washed curd, Colby, stirred curd cheese and Monterey Jack. All must contain at least 50% fat in dry matter (FDM). Modifications in the process for making Cheddar led to the development of the other three varieties. Washed curd cheese is prepared as Cheddar through the milling stage, when the curd is covered with cold water for 5 to 30 minutes. Washing increases moisture to a maximum of 42%. Stirred curd cheese has practically the same composition as Cheddar but has a more open texture and shorter (less elastic) body. It is manufactured as Cheddar except that agitation of cooked curd particles is used to promote whey drainage, and the Cheddars and milling steps are eliminated. Colby cheese and Monterey Jack cheese are manufactured the same way as stirred curd except that water is added to wash and cool the curd when most of the whey has been drained away, thus increasing the moisture content to a maximum of 40% for Colby cheese and 44% for Monterey Jack cheese.

"Pasta filata-type cheese" as used herein means a type of cheese having a plastic, pliable, homogeneous, stringy structure. The pasta filata cheeses are traditionally made by producing curds and whey, draining the whey and immersing the curd in hot water or hot whey and working, stretching, and molding the curd while it is in a plastic condition. The principal varieties of pasta filata cheeses are: cociocavallo, provolone, provolette, pizza cheese, mozzarella, provole, scamorze, and provatura. The most well known example of pasta filata-type cheese is mozzarella. In the U.S., the standards of identity of the code of federal regulations subdivide mozzarella cheeses into: "mozzarella", "low moisture mozzarella," "part skim mozzarella", and "low moisture part skim mozzarella." As defined by food and drug administration (FDA) regulations, mozzarella has a moisture content of more than 52 but not more than 60 weight percent and fat in dry matter (FDM) of not less than 45 percent by weight. The low moisture mozzarella has moisture content of more than 45 but not more than 52 weight percent and FDM of not less than 45 weight percent. The part skim mozzarella contains more than 52 but not more than 60 percent of moisture by weight and has FDM of less than 45 but not less than 30 percent. The low moisture part skim mozzarella contains more than 45 but not more than 52 percent of moisture by weight and has FDM of less than 45 but not less than 30 percent.

"UT cheese" means a cheese produced by a process in which milk is processed by ultratiltration and usually diafiltration to remove water and lactose, but leave the whey proteins in the UF retentate. Fermentation or direct acidification, followed by further water removal, results in UF cheese. If fermentation is used, a starter culture is added to the UF retentate. Fermented UF retentates often contain about 55-60% moisture, and are evaporated to less than 40% moisture, and most preferably to about 30-35% moisture in the final UF cheese. The final evaporation step may be made easier if the retentate is preheated to a temperature of between about 140° F. and about 212° F. before being evaporated, as disclosed in U.S. Pat. No. 5,356,639, which is incorporated herein by reference. As also disclosed in the '639 patent, rennet may be added to the retentate prior to evaporation, and possibly at the same time as the starter culture, to make a product more suitable for conversion to processed cheese. However, the amount of rennet may be sufficient to coagulate the retentate, contrary to the statement on col. 15 lines 58-59 of the '639 patent.

"Processed cheese" as used herein generally refers to a class of cheese products that are produced by comminuting, mixing and heating natural cheese into a homogeneous, plastic mass, with emulsifying agents and optional ingredients, depending on the class of processed cheese produced. The comminuted cheese is blended and sent to cookers or the like, which commonly heat the mass to a temperature of 150°-210° F., preferably 165°-190° F. During cooking, fat is stabilized with the protein and water by the emulsifying agents, which are typically citrate or phosphate salts, usually at a level of about 3%. The emulsifying agent causes the protein to become more soluble. Under these circumstances a stable emulsion of protein, fat and water occurs to provide a smooth, homogeneous mass. The hot mass is packaged directly, or formed into slices and packaged. There are four main classes of processed cheese in the U.S.: pasteurized process cheese, pasteurized process cheese food, pasteurized process cheese spread and pasteurized process cheese product. All four classes of processed cheese are made with emulsifying agents. Standards of identity apply to pasteurized processed cheese and are established by the FDA. By those standards, whey solids, including whey proteins, may not be added to the pasteurized process cheese.

"Emulsifying agents" as used herein means emulsifying agents used in the making of processed cheese. These include one or any mixture of two or more of the following inorganic salts: monosodium phosphate, disodium phosphate, dipotassium phosphate, trisodium phosphate, sodium metaphosphate, sodium acid pyrophosphate, tetrasodium pyrophosphate, sodium aluminum phosphate, sodium citrate, potassium citrate, calcium citrate, sodium tartrate, and sodium potassium tartrate. In processed cheese, these emulsifying agents act as calcium sequestering (or chelating) agents.

"Natural cheese" as used herein means a cheese that does not contain emulsifying agents. Conventional cheeses (containing very small amounts of whey proteins) and cheeses made using an UF process (containing high levels of whey proteins) are the usual varieties of natural cheeses.

"Cheese material" as used herein includes conventional cheese, UF cheese and intermediate materials in the conventional or UF cheese making process. The most common cheese materials used in the present invention are cheese curds, comminuted natural cheese and UF cheese. Cheese materials also include cheese made from other than fresh milk. For example, cheese material may be made from dairy liquids such as reconstituted dry milk powder. The fat content of the milk or other dairy liquid may be adjusted before making the cheese material. Preferably the cheese material will have a pH of less than 5.6, a moisture content of less than 60% and contain one or more coagulating agents, such as a protease, and most commonly rennet. Preferably, the cheese material will contain at least 15% protein by weight, more preferably at least 20% protein by weight and preferably at least 10% casein by weight.

TEST PROCEDURES

The present invention and the benefits thereof are most easily understood when described in terms of several standards for evaluating the firmness and melt properties of processed cheese.

Schreiber Melt Test

The L. D. Schreiber melt test is a well-known and accepted standardized test for determining the melt properties of cheese. The test uses a kitchen oven and a standardized piece of cheese, and measures the size of the cheese piece after it is melted. The instructions for the procedure, as used in tests with results reported below, are as follows:

1. Preheat oven to 450° F. (232.2° C.).
2. Slice cheese 3/16 thick (5 mm). If cheese is already sliced, use 2-3 slices to get closest to the 3/16 thickness.
3. Cut a circle out of the cheese slice using a copper sampler with a diameter of 39.5 mm.
4. Center the cheese circle in a thin wall 15×100 mm petri dish, cover and place on the center rack of the oven. Do this quickly so the oven temperature does not drop below 400° F. (204.4° C.).
5. Bake for 5 minutes and remove. Up to 4 dishes may be done at the same time.
6. Once cooled, the melt is measured on the score sheet.

The score sheet comprises a series of concentric circles with increasing diameters. The first circle has a diameter of 40.0 mm. Each succeeding circle is 6.5 mm larger is diameter. The melted cheese receives a score of 1 if it fills the first circle, a score of 2 if it fills the second circle, etc. As used herein, the scores include a "+" (or "−") indicating that the cheese was slightly larger (or smaller) than the indicated score ring. A cheese with an acceptable Schreiber melt test will score 3 or above.

Mettler Melt Test

The meltabilities of cheeses can also be compared using an apparatus for determination of dropping point or softening point, such as the Mettler FP 800 thermosystem. In such an apparatus, the temperature at which a plug of cheese falls through an orifice is measured. In general, cheeses with acceptable melt characteristics have a Mettler melt temperature below 200° F. Cheeses exhibiting non-melt characteristics will not melt at 230° F., which is the shut-off temperature of the Mettler FP 800 instrument as set up for this test, which prevented the temperature from rising too high and burning non-melting samples inside the instrument. The Mettler FP 800 instrument was set up with the start temperature at 100.0° F. and the heating temperature rate at 5.0° F./minute.

The instructions for sample preparation are as follows:

1. The sample cup (middle piece) is pushed through the cheese sample until the sample extruded from the small top hole of the cup.

2. A knife is used to carefully trim around the cup and square off cheese at the top and bottom.

3. Samples of cheese to be prepared are kept in airtight bags to prevent drying out. Samples of cheese that are prepared for analysis in their cups are kept in a petri dish to prevent drying out if they are not to be analyzed immediately.

4. The bottom holder and top holder of the sample cup are assembled with the center section.

5. The entire assembly, using the top holder stem, is placed in the oven and gently turned until it is seated on the bottom of the oven.

6. After the sample is placed in the instrument, the run/stop button is pushed. At this point there is a 30 second countdown while the oven temperature equilibrates at 100° F. The oven temperature will begin to rise and will shut off at the softening point of the cheese or at 230° F., in case the cheese does not soften and flow. The softening point reading will be printed on paper, or the end temperature (230° F.) will be printed if the cheese does not soften.

7. A fan inside the oven will turn on to bring the temperature back to 100° F. or below. When the fan has turned off, the entire assembly is removed from the oven and disassembled. The sections are cleaned using the scraper provided for the cup and tweezers to remove cheese from the bottom holder.

Instron Firmness Measurement

The firmness of the cheese is measured by an Instron Tester (Model 5542 Canton, Mass.). The cheese is cut into chunk size (2"×3"×4") and tempered at 40° F. overnight. A compressive loading force is applied to the cheese sample with a McCormic Fruit Tester plunger (8 mm diameter) attached to a load cell (500 Newton). The maximum force (kgf) recorded for the plunger as it travels downward (at a speed of 330 mm/min.) with a penetration depth of 11 mm into cheese is defined as the firmness of the cheese.

Because the moisture content of processed cheese has a significant impact on the Instron firmness measurement, it is useful to compare firmness data of different processed cheeses on a comparable moisture content basis. To do this, a correction factor of 0.2 kgf for each 1% moisture decrease has been found to be fairly accurate. Therefore, this correction factor is used herein to determine firmness at a corrected moisture content of 40%. For example, a processed cheese with actual moisture at 39.8% and a measured Instron firmness of 1.0 kgf would have an Instron firmness value corrected to 40% moisture of 0.96 kgf.

Transglutaminases are enzymes that catalyze the transfer of the γ-carboxamide group of a glutaminyl residue in a protein or peptide to the ϵ-amino of a lysyl residue of the same or a different protein or peptide, thereby forming a γ-carboxyl ϵ-amino cross-link. Transglutaminases have a broad occurrence in living systems, and may be obtained, for example, from microorganisms such as those belonging to the genus *Streptoverticillium, Bacillus subtilis*, various *Actinomycetes* and *Myxomycetes*, or from plants, fish species, and mammalian sources including pig liver and the blood clotting protein activated Factor XIII. In general, transglutaminases from animal sources require calcium ions for activity. Recombinant forms of transglutaminase enzymes may be obtained by genetic engineering methods as heterologous proteins produced in bacterial, yeast, and insect or mammalian cell culture systems. The principal requirement of any transglutaminase employed in the instant invention is that it have the cross-linking activity discussed above. Any enzyme having transglutaminase activity may be employed in the methods of the present invention. In a preferred embodiment, the transglutaminase is obtained from the genus *Streptoverticillium*.

Transglutaminase activity may be determined using known procedures. One such colorimetric procedure uses benzyloxycarbonyl-L-glutaminyl-glycine and hydroxylamine to form a γ-carboxyl-hydroxamic acid if transglutaminase is present. An iron complex of the hydroxamic acid can be formed in the presence of ferric chloride and trichloroacetic acid. Using the absorbance at 525 mm with appropriate standards, the activity of enzyme present may be determined. Activity in the present invention is determined and defined as follows. A reaction system containing benzyloxycarbonyl-L-glutamylglycine and hydroxylamine as substrates is reacted with transglutaminase in a tris buffer (pH 6.0) at a temperature of 37° C., and the hydroxamic acid formed is transformed into an iron complex in the presence of trichloroacetic acid. Then, the absorbance at 525 nm is measured, and the amount of hydroxamic acid is calculated using a calibration curve. Thus, the amount of enzyme by which 1 μmol of hydroxamic acid is formed in 1 minute is defined as 1 unit (1 U) of transglutaminase activity. The complete procedure for determining activity is disclosed in U.S. Pat. No. 5,156,956, which is hereby incorporated by reference.

There are three presently preferred embodiments of the invention. These embodiments are explained in detail by the examples that follow. In the first embodiment, transglutaminase is mixed with the comminuted cheese during the normal processed cheese manufacturing process, but this mixture is given time to react before it is heated up to the temperature at which processed cheese is pasteurized. In the second embodiment, transglutaminase is added to cheese curds as the cheese curds are packed into blocks or barrels. The transglutaminase can then cross link proteins in the cheese curds while the curds knit together as the cheese is aged before it is comminuted and used to make processed cheese. In the third embodiment, transglutaminase is added to UF cheese as it is manufactured and before it is placed in barrels. Again, the transglutaminase can cross link proteins while the UF cheese is aged before being made into processed cheese.

All three of these preferred embodiments are common in that transglutaminase is allowed to react on, and cross link the proteins in, a cheese material rather than on a dilute system such as milk or other dairy liquid. As noted above, the cheese material will preferably have a moisture content of less than 60%, and more preferably less than 50%. The cheese material will also preferably have a pH of less than 5.6, and more preferably less than 5.3. However, a UF cheese with a pH of between 5.6 and 6.0, and even as high as 6.6, may also be used as a cheese material in some embodiments of the invention. It is typical that the transglutaminase will be mixed with the cheese material after the cheese material has already been formed with those moisture and pH properties. However, as explained below, there are modifications of the process in which the transglutaminase may be mixed with a material that then later has those properties. The key factor is that during the majority of the time that the transglutaminase is allowed to react on the protein in the cheese material, the moisture content is preferably less than 60%. In this fashion, the protein will be concentrated and the amount of transglutaminase needed to catalyze the cross-linking reaction can be minimized.

It is possible that other ingredients that will eventually be in the processed cheese may be mixed with the transglutaminase as it is allowed to cross-link the proteins. However, such ingredients are optional, and added only as a matter of convenience or for some reason unrelated to the cross-linking reaction. For example salt, such as sodium chloride, is often added to curds before the curds are packed in blocks or barrels. The transglutaminase may be mixed with the salt or otherwise added to the curds with the salt, the salt being an optional first other ingredient in the second preferred embodiment of the invention. Also, the cheese material in the preferred embodiments has not been melted prior to the cross-linking reaction.

After the transglutaminase and cheese making material have been mixed, conditions are provided under which the cross-linking reaction can favorably occur. Commercially available ACTIVA TG-TI transglutaminase sold by Ajinomoto U.S.A. Inc. has high activity in a range of pH from 5-8. As with all reactions, the higher the temperature the greater the reaction speed. However, the commercial enzyme activity decreases gradually above about 50° C. (122° F.) and drops to a fairly low level at 60° C. (140° F.). At 80° C. (176° F.) the enzyme is deactivated within 1 minute. Thus there is a balance between stability and reaction rate that must be made. As a result, the optimum temperature range for the commercial enzyme is between about 20° C. (78° F.) and about 60° C. (140° F.). However, if sufficiently long reaction times are available, lower temperatures may be used. The commercially available enzyme is active at 15° C. (59° F.) and even at 5° C. (41° F.). The preferred reaction temperature are thus in the range of between about 50° F. and about 120° F.

The reaction time, temperature and pH must be sufficient to allow at least a portion of the proteins in the cheese material to become cross-linked. Of course, a high degree of cross-linking is desired. Normally the reaction time will be shorter in the first preferred embodiment of the invention, and longer in the second and third preferred embodiments. It would be preferable to give the enzyme plenty of time to react. However, it is cost prohibitive to significantly lengthen the manufacturing time for making processed cheese. Of course, higher levels of enzyme can be added to achieve a sufficient reaction, but again the enzyme cost is currently a considerable factor that precludes this option. In the first preferred embodiment of the invention the reaction time will preferably be in the range of about 10 minutes to about 3 hours, more preferably between about 1½ and about 2½ hours, and most preferably about 2 hours. In this embodiment the enzyme will be mixed at a ratio of between about 0.2 and about 10 units per gram of protein. In the second and third preferred embodiments of the invention, the enzyme can be used at lower levels, preferably less than 5 units per gram of protein. The reaction time for these embodiments of the invention will typically be greater than 24 hours, and more preferably greater than two weeks. These long reaction times coincide with the periods that conventional cheese and UF cheese are normally aged before being used to make processed cheese. Thus in these embodiments, the time it takes to manufacture process cheese is not lengthened at all.

The end of the reaction time occurs when the enzyme is deactivated, which preferably occurs during the normal practice of making processed cheese. Government regulations require the processed cheese to be heated to a temperature of 150° F., but it is more common that it is heated to 170° F. or even up to 210° F. As noted above, these temperatures will deactivate the commercially available transglutaminase.

In the preferred embodiments of the invention, the mixture is preferably essentially free of emulsifying agents during the reaction time. Thus, the preferred methods of the invention include the step of mixing emulsifying agents with the mixture of cheese material and transglutaminase after the reaction time has occurred. The emulsifying agents are those normally used in making processed cheese. Sodium citrate, trisodium phosphate and disodium phosphate are the presently preferred emulsifying agents.

Typically additional processed cheese ingredients will be added along with the cheese material having cross-linked proteins to make the processed cheese. These second other optional ingredients typically include sorbic acid, sodium chloride, dry cream, concentrated milk fat, whey powder, whey protein concentrate, milk protein concentrate, non-fat dry milk, buttermilk powder and water.

As will be seen in the examples below, the optional second ingredients in the second and third preferred embodiments may include an additional cheese material that has not been treated with transglutaminase.

As will also be seen in the examples below, the finished processed cheese will typically have a moisture content of between about 30% and about 60%, a fat content of between about 10% and about 40%, and a protein content of between about 10% and about 30%. The processed cheese of the present invention will preferably have a Mettler melt temperature of between about 120° F. and about 200° F., more preferably between about 120° F. and about 150° F. and a Schreiber melt score of at least 3 and more preferably at least 5.

It has been found that the firmness of processed cheese can be affected by a number of factors unrelated to the cross linking of proteins. For example, it has been found that processed cheese made in a pilot plant typically has an Instron firmness of about 0.5 kgf less than that of processed cheese made on commercial equipment. It is believed that the sheer applied to the cheese material when making processed cheese has a big impact on the resulting firmness, and that commercial scale equipment usually involves higher sheer rates and greater firmness. Also, the age of the cheese used to make the processed cheese has a major impact on firmness. The use of younger cheese will result in greater firmness. While the processed cheese of the present invention will generally have an Instron firmness, corrected to 40% moisture, of at least 1 kgf, the preferred processed cheese of the present invention made in commercial equipment, after being cooled for 3 days at 40° F., will have an Instron firmness, corrected to 40% moisture, of at least 1.5 kgf. More preferably the Instron firmness, corrected to 40% moisture, will be at least 1.8 kgf, and most preferably at least 2.0 kgf. In any event, it is preferred that the cross linking increase the firmness of processed cheese to be at least 5% greater than the firmness of processed cheese made by the same procedure but without the cross-linking enzyme. The following examples show how such a comparison can be made. It is more preferred that the firmness increase by at least 10%. With some preferred embodiments of the invention, firmness will be increased by more than 25% and even 30%.

EXAMPLE 1

Treating Cheese Blend with Transglutaminase Shortly Before Converting it into Processed Cheese A ten pound processed cheese formula with a target finished product composition of 39.5% moisture, 32.0% fat and 2.3% salt is shown in Table 1 below:

TABLE 1

| Cheese/Ingredient | Processed Cheese (10 lbs.) Weight (lb) |
|---|---|
| Barrel Cheese (1.5 months old) | 4.24 |
| UF Cheese (1 month old) | 2.08 |
| Trisodium Phosphate | 0.013 |
| Sodium Citrate | 0.348 |
| Sorbic Acid | 0.02 |
| Salt | 0.117 |
| Dry Cream | 0.231 |
| Concentrated Milk Fat | 1.08 |
| Whey Powder | 0.37 |
| Water | 1.50 |
|  | 10 lbs |

The above processed cheese formula was made using two types of cheese: conventional barrel cheese and the UF cheese. The conventional barrel cheese (500 lbs) was purchased from Associated Milk Producers, Inc. (Paynsville, Wis.). The finished barrel cheese met the standards of Cheddar cheese for manufacturing as defined by 21 C.F.R. §133.114 (2001). The UF cheese was made using the Jameson et al. process as disclosed in U.S. Pat. No. 5,356,639; with the modification that rennet was added. The UF cheese was prepared by ultrafiltering and diafiltering milk to produce a retentate, adding salt to the retentate, fermenting the retentate and evaporating the fermented retentate to produce cheese containing all the casein and whey protein of the original milk. The fermented retentate was treated with rennet in an amount sufficient to coagulate the fermented retentate prior to the evaporation. Also, the fermented retentate was preheated to a temperature of between about 170° F. and about 190° F. before being introduced into the evaporator.

The transglutaminase enzyme preparation (ACTIVA TG-TI) was obtained from Ajinomoto U.S.A. Inc. (Teanack, N.J.). The ACTIVA TG-TI contains about 100 units of activity per gram. ACTIVA TG-TI contains 99% maltodexrin and 1% transglutaminase enzyme.

A cheese blend containing the ground barrel cheese (4.24 lbs), UF cheese (2.08 lbs) and water (1.5 lbs) was mixed with 35 grams of ACTIVA TG-TI in a 10 lb size Rietz cooker for 2 hours at 85° F. with the auger speed set at 1. This provided time for the transglutaminase to cross link at least a portion of the proteins in the cheese blend. The calculated ratio of ACTIVA TG-TI (35 gram) to cheese blend (7.82 lbs) was estimated at ~1.0%, and the ratio of transglutaminase cross-linking enzyme to protein was estimated at ~5.13 units per gram of protein. A control processed cheese was made using the same cheese blend except 35 grams of maltodextrin were used to replace the 35 grams of ACTIVA TG-TI.

After the 2 hour, 85° F. mixing, other ingredients were added to the cooker and the temperature was increased as in a normal processed cheese manufacturing process. Both control and transglutaminase-treated cheese blends were used to make control and inventive processed cheese according to the processed cheese formula (Table 1). The control and inventive processed cheese mixtures were each cooked to 170° F. with indirect steam jacket heating with the auger speed set at 4. It took approximately 10 minutes to reach the 170° F. temperature in each case. The indirect steam heat was then turned off. The finished processed cheeses had a homogeneous, plastic, molten consistency when they were discharged at 170° F. to 14 oz. tubs. The cook temperature of 170° F. also provided the necessary heat to deactivate the transglutaminase in the inventive cheese blend. The finished processed cheeses were cooled at 40° F. for 3 days. The proximate composition, melt properties, and Instron firmness of the finished processed cheeses are shown in Table 2 below:

TABLE 2

| Cheese Blend | Processed Cheese Composition | | | | | | | |
|---|---|---|---|---|---|---|---|---|
|  | % $H_2O$ | % Fat | % Salt | pH | SFI Melt Score | Mettler Temp (° F.) | Instron Firmness kgf* | % Increase in Firmness |
| 1. Control | 39.82 | 32.0 | 2.72 | 5.85 | 5 | 131 | 1.015 | — |
| 2. Transglutaminase treated (~1% ACTIVE TG–TI) | 39.48 | 32.5 | 2.44 | 5.87 | 4+ | 148 | 1.441 | 41.97 |

*Instron firmness readings corrected to 40% moisture.

The composition differences between the control and transglutaminase-treated processed cheeses reflect normal variations due to cheese ingredients and measurement error. The data in Table 2 clearly demonstrates that the transglutaminase-treated cheese blend of Example I resulted in a significant increase in firmness (+41.9%) as compared to the control.

EXAMPLE 2

Treating Cheese Curd with Transglutaminase During the Manufacture of the Conventional Cheddar Cheese Cheddar cheese in a 40 lb block form was made at Carr Valley Cheese Co., Inc., (Lavelle, Wis.) following the conventional milled curd process. A commercial transglutaminase enzyme preparation, ACTIVA TG-TI, was first mixed with salt and then applied to the milled curd during the regular salting step of the make process. The curd/salt/ACTIVA TG-TI ratios were set at 1000 lbs curd/27.3 lbs salt/2.5 lbs ACTIVA TG-TI.

The calculated ratio of ACTIVA TG-TI to the curd was ~0.25%. The ratio of transglutaminase activity to protein was estimated at ~1 unit per gram of protein. A control Cheddar cheese was made in an identical fashion compared to the cheese made with the transglutaminase treatment except maltodextrin was used to replace ACTIVA TG-TI.

The control and AVTIVA TG-TI treated cheese curd were then each pressed in 40 lb hoops overnight and packed/stored in a 40° F. cooler until their use in the processed cheese formulation. The produced Cheddar cheeses had the following proximate composition:

TABLE 3

| Cheddar Cheese (40 lb block) | Composition | | | |
| --- | --- | --- | --- | --- |
| | % H₂O | % Fat | % Salt | pH |
| 1. Control | 37.47 | 33 | 1.74 | 4.97 |
| 2. Transglutaminase treated (~0.25% ACTIVA TG–TI) | 36.82 | 34 | 1.72 | 5.00 |

Both control and transglutaminase-treated Cheddar cheeses had a typical Cheddar cheese composition with acceptable flavor and texture. Both the control and transglutaminase-treated Cheddar cheeses were made into processed cheese as described below in conjunction with Example 4.

EXAMPLE 3

Treating Fermented Milk Retentate with Transglutaminase During the Manufacture of UF Cheese The UF cheese was manufactured according to the modified Jameson et al. process disclosed in U.S. Pat. No. 5,356,639 described in Example 1.

An ACTIVA TG-TI suspension (~28%) was first prepared by dispersing 12 lbs ACTIVA TG-TI in 5 gallons of cold water. The prepared ACTIVA TG-TI solution was then injected into the feed stream of fermented retentate immediately after the preheating step (which was at 170° F.-190° F.) and before reaching the evaporator. The flash evaporation in the evaporator reduced the temperature of the cheese material to about 120° F. so that the transglutaminase was not deactivated. Evaporation was completed in a swept-surface evaporator with a product exit temperature of 90° F.-95° F. The feed rate of the fermented retentate to the evaporator was set to produce ~4900 lbs. cheese/hr. The injection rate of the ACTIVA TG-TI solution (~28%) was set at 5 gallons/hr.

The resulting UF cheese was calculated as containing (after evaporation) ~0.25% active ACTIVA TG-TI. The ratio of transglutaminase activity to protein was calculated to be ~1.09 units/gram of protein. A control UF cheese was prepared using identical feed materials and processing conditions except that an injection of 28% maltodextrin was used to replace the ACTIVA TG-TI solution.

Both control and transglutaminase-treated UF cheeses were packed in 500 lbs. barrels and stored in a cooler at ~40° F. until their use in the processed cheese formulation. The produced UF cheeses had the following proximate composition:

TABLE 4.

| UF Cheese (500 lbs. Barrel) | Composition | | | |
| --- | --- | --- | --- | --- |
| | % H₂O | % Fat | % Salt | pH |
| 1. Control | 33.23 | 38.0 | 1.76 | 5.51 |
| 2. Transglutaminase treated (~0.25% ACTIVA TG–TI) | 32.82 | 37.5 | 1.78 | 5.58 |

Both control and transglutaminase-treated UF cheeses had a typical UF cheese composition with acceptable flavor and texture. Both the control and transglutaminase-treated UF cheeses were made into processed cheese as described below in conjunction with Example 4.

EXAMPLE 4

Processed Cheese made from Cheddar Cheese (Example 2) and UF Cheese (Example 3)

Cheddar cheese (aged 28 days with approximately 0.25% transglutaminase) from Example 2 and UF cheese (aged 22 days with approximately 0.25% transglutaminase) from Example 3 were cooked into process cheese following the formula of Table 5.

TABLE 5

| Cheese/Ingredient | Processed Cheese (10 lbs) Weight (lbs) |
| --- | --- |
| Cheddar Cheese (28 days, Example 2) | 4.24 |
| UF Cheese (22 days, Example 3) | 2.08 |
| Trisodium Phosphate | 0.013 |
| Sodium Citrate | 0.348 |
| Sorbic Acid | 0.02 |
| Salt | 0.117 |
| Dry Cream | 0.231 |
| Concentrated Milk Fat | 1.08 |
| Whey Powder | 0.37 |
| Water | 1.50 |
| | 10 lbs |

To demonstrate the impact of transglutaminase-treated cheese on the finished processed cheese firmness, four 10 lb cook experiments were conducted using different combinations of control and transglutaminase-treated cheese materials as outlined below.

| | Cheese type used in processed cheese formulation | |
| --- | --- | --- |
| Cook ID | Cheddar (Example 2) | UF Cheese (Example 3) |
| 1 | Control | Control |
| 2 | Transglutaminase | Control |
| 3 | Control | Transglutaminase |
| 4 | Transglutaminase | Transglutaminase |

A mixture of the ground Cheddar cheese (Example 2 or control) and UF cheese (Example 3 or control) were blended with other ingredients as shown in the above formula (Table 5). The blend mixtures were cooked in a 10 lb Rietz cooker with indirect steam jacket heating at an auger speed setting of 4. The finished processed cheeses were heated to 170° F. in a period of about 10 minutes to achieve homogeneous, molten, plastic body and immediately discharged into 14 oz. tubs for cooling (~40° F., 3 days). Cook ID 2, 3 and 4 thus relate to Examples 2, 3 and 4, respectively. The proximate composition, melt properties and Instron firmness of the processed cheeses are shown in Table 6.

TABLE 6

| | Cheese Type | | | | | | | | Mettler | Instron |
|---|---|---|---|---|---|---|---|---|---|---|
| Cook ID | Cheddar | UF Cheese | % H$_2$O | % Fat | % Salt | pH | SFI Melt | | Temp (° F.) | Firmness kgf* |
| 1 | Control | Control | 40.45 | 33.0 | 2.46 | 5.78 | 7+ | | 125 | 1.026 |
| 2 | Transgl. | Control | 40.46 | 33.5 | 2.58 | 5.82 | 5+ | | 134 | 1.317 |
| 3 | Control | Transgl. | 40.70 | 34.5 | 2.48 | 5.81 | 5+ | | 134 | 1.152 |
| 4 | Transgl. | Transgl. | 40.49 | 33.5 | 2.58 | 5.81 | 5+ | | 136 | 1.388 |

*Instron firmness corrected to 40% moisture.

From the Instron firmness data in Table 6, the impact of 0.25% transglutaminase-treated Cheddar and UF cheese on processed cheese firmness was calculated and is shown in Table 7.

TABLE 7

| Processed Cheese Firmness Comparison | Instron* Firmness Increase | Impact due to |
|---|---|---|
| 1. Cook 2 vs. Cook 1 | 28.36% | 0.25% ACTIVA TG-TI treated Cheddar |
| 2. Cook 4 vs. Cook 3 | 20.48% | 0.25% ACTIVA TG-TI treated Cheddar |
| 3. Cook 3 vs. Cook 1 | 12.28% | 0.25% ACTIVA TG-TI treated UF cheese |
| 4. Cook 4 vs. Cook 2 | 5.39% | 0.25% ACTIVA TG-TI treated UF cheese |
| 5. Cook 4 vs. Cook 1 | 35.28% | 0.25% ACTIVA TG-TI treated Cheddar cheese and UF cheese |

*1. $\frac{1.317 - 1.026}{1.026} \times 100 = 28.36\%$

*2. $\frac{1.388 - 1.152}{1.152} \times 100 = 20.48\%$

*3. $\frac{1.152 - 1.026}{1.026} \times 100 = 12.28\%$

*4. $\frac{1.388 - 1.317}{1.317} \times 100 = 5.39\%$

*5. $\frac{1.388 - 1.026}{1.026} \times 100 = 35.28\%$

The results reported in Table 7 demonstrate that the transglutaminase-treated Cheddar cheese (0.25% ACTIVA TG-TI) would contribute ~20.48 to 28.36% firmness increase in the processed cheese formula studied. The data also demonstrates that the transglutaminase-treated UF cheese (0.25% ACTIVA TG-TI) would provide ~5.39% to 12.28% firmness increase in the processed cheese formula studied. The impact of both transglutaminase-treated Cheddar cheese (0.25% ACTIVA TG-TI) and UF cheese (0.25% ACTIVA TG-TI) resulted in even greater firmness increase (~35.28%) in the processed cheese formula studied.

EXAMPLE 5

Commercial Scale Production of Processed Cheese Containing the Transglutaminase-Treated UF Cheese (Example 3)

The UF cheese from Example 3, (containing approximately 0.25% ACTIVA TG-TI) and a conventional Cheddar cheese were ground and blended with the other ingredients according to the following formulation (Table 8). A control batch of processed cheese was made using the control UF cheese from Example 3.

TABLE 8

| Cheese/Ingredient | Weight (lbs) |
|---|---|
| UF Cheese (Example 3) | 3147 |
| Young Cheddar | 3560 |
| Medium Cheddar | 173 |
| Sodium Citrate | 297 |
| Concentrated Milk Fat | 594 |
| Non-Fat Dry Milk | 495 |
| Whey Powder | 100 |
| Carotenal Color | 8.6 |
| Salt | 127 |
| Sorbic | 20 |
| Water | 1702 |
| | 10223.6 |

Blend 1 contained the control UF cheese (0.25% maltodextrin, Example 3). Blend 2 contained the transglutaminase-treated UF cheese (0.25% ACTIVA TG-TI, Example 3). All other cheese/ingredients in blends 1 and 2 were the same.

The ground cheese and other ingredient mixture was blended for 30 minutes before being fed continuously into a commercial size swept surface cooker with indirect steam jacket heating. The blend mixture was cooked to 190° F. and discharged with a molten plastic homogeneous body. The molten process cheese was quickly cooled down to below 60° F. The finished process cheese was further cooled down (<40° F.) inside the final packages during distribution.

The proximate composition, melt properties and Instron firmness of the finished process cheeses are shown in Table 9.

TABLE 9

| | | Process Cheese | | | | | | | |
|---|---|---|---|---|---|---|---|---|---|
| Blend ID | UF Cheese Type | % H$_2$O | % Fat | % Salt | pH | SFI Melt | Mettler Melt (° F.) | Instron Firmness kgf* | % Instron Firmness ** |
| 1 | Control | 39.16 | 30.0 | 2.64 | 5.99 | 3+ | 146 | 2.388 | — |
| 2 | Transglutaminase treated (~0.25% ACTIVA TG-TI) | 38.95 | 31.0 | 2.44 | 6.00 | 4 | 156 | 2.605 | 9.08 |

*Instron firmness collected to 40% moisture

** $\dfrac{2.605 - 2.388}{2.388} \times 100 = 9.08\%$

The higher Instron firmness results in Table 9 compared to Table 6 reflect the fact that processed cheese made in commercial scale equipment is generally firmer than processed cheese made in pilot plant equipment, and the fact that the cheese used in Example 5 had a younger average age than the cheese used in Examples 1-4. The test results reported in Table 9 demonstrate that the transglutaminase-treated UF cheese (0.25% ACTIVA TG-TI) provided ~9.08% firmness increase in the processed cheese formula studied.

An increased firmness in processed cheese has numerous benefits. A firmer product can be packaged at higher rates of speed. Manufacturing steps are also easier to perform when the processed cheese is firm. The packaged product maintains its shape, resisting cold flow. The moisture content of the product can be increased (resulting in a lower product cost) if the firmness of the product can otherwise be maintained. The preferred embodiment of the present invention provides a mechanism whereby the firmness of the processed cheese can be improved without adding significantly to the time required to make the processed cheese, and while maintaining acceptable melt properties. Further, the amount of transglutaminase required to improve the firmness is minimized by using it in a concentrated protein composition.

It should be appreciated that the method and products of the present invention are capable of being incorporated in the form of a variety of embodiments, only a few of which have been illustrated and described above. The invention may be embodied in other forms without departing from its spirit or essential characteristics. For example, while the transglutaminase was mixed with the cheese blend in the cooker in Example 1, commercial use of that embodiment of the invention would likely involve mixing the transglutaminase with the cheese blend in a different vessel, such as a blender, and later placing the mixture into the cooker, with the time for the cross-linking reaction occurring in the blender, the cooker or even in an intermediate vessel.

As noted above, the other processed cheese ingredients, particularly the emulsifying agents, are preferably added after the cross-linking reaction has progressed. Alternatively, these other ingredients could be added before the time for the cross-linking reaction has elapsed. Also, if a preheating step were not used in the UF cheese-making process, the transglutaminase could be added at an earlier point in the process, even to the initial milk after it was pasteurized, because the transglutaminase would be retained with the milk proteins in the ultrafiltration and diafiltration steps. Also, the UF cheese could be made by direct acidification rather than fermentation, and rennet may be added to the retentate prior to the fermentation or not used at all.

The above examples use Cheddar and UF cheese, but other cheeses can be used, particularly other American-type cheeses and pasta filata-type cheeses. The described embodiments are thus to be considered in all respects only as illustrative and not restrictive, and the scope of the invention is, therefore, indicated by the appended clams rather than by the foregoing description. All changes that come within the meaning and range of equivalency of the claims are to be embraced within their scope.

The invention claimed is:

1. A method of making a processed cheese with improved firmness comprising:
    a) mixing a protein cross-linking enzyme with a cheese material having a pH of less than 5.6 and a moisture content of less than 60% to form a mixture;
    b) providing temperature and pH conditions and allowing time for the enzyme to react with protein in the mixture to cross link at least a portion of the protein; and
    c) combining one or more emulsifying agents with the mixture after said time to form a combination, and heating the combination to thereby produce processed cheese.

2. The method of claim 1 wherein the cheese material comprises cheese curds and the protein cross-linking enzyme is mixed with the cheese curds before the cheese curds are packed to form cheese blocks or barrel cheese, the cheese blocks or barrel cheese later being used to make the processed cheese.

3. The method of claim 1 wherein the cheese material comprises comminuted cheese and the protein cross-linking enzyme is mixed with the comminuted cheese during a processed cheese manufacturing process.

4. The method of claim 3 wherein the combination is heated to a temperature of at least 170° F. to produce the processed cheese, and the cross-linking enzyme is allowed to react for a period of between about 10 minutes and about 3 hours at a temperature of between about 50° F. and about 120° F. before the temperature of at least 170° F. is reached.

5. The method of claim 4 wherein the cross-linking enzyme is allowed to react for a period of between about 1½ and about 2½ hours before the temperature of at least 170° F. is reached.

6. The method of claim 3 wherein the comminuted cheese comprises cheese that has been aged at least 24 hours.

7. The method of claim 3 wherein the comminuted cheese comprises cheese that has been aged for at least 2 weeks.

8. The method of claim 1 wherein the mixture is at a temperature of between about 50° F. and about 120° F. during the time the cross-linking enzyme is allowed to react.

9. The method of claim 1 wherein the combination is heated to a temperature of between about 150° F. and about 210° F. to produce the processed cheese.

10. The method of claim 1 wherein the cheese material is made by ultrafiltration and diafiltration of milk to produce a retentate, fermenting the retentate and removing water from the fermented retentate, and the cross-linking enzyme is mixed with the retentate prior to the step of removing water but is allowed to react after the moisture of the fermented retentate is reduced to less than 60%.

11. The method of claim 1 wherein the protein cross-linking enzyme comprises transglutaminase.

12. The method of claim 1 wherein the ratio of cross-linking enzyme to protein in the mixture is between about 0.2 units per gram of protein and about 10 units per gram of protein.

13. The method of claim 1 wherein the processed cheese comprises about 30% to about 60% moisture; about 10% to about 40% fat and about 10% to about 30% protein.

14. The method of claim 1 wherein the processed cheese, after being cooled for 3 days at 40° F., has a firmness, corrected to 40% moisture, of at least 1.5 kgf.

15. The method of claim 1 wherein the processed cheese has a firmness of at least 5% greater than the firmness of a processed cheese made by the same procedure but without the cross-linking enzyme.

16. The method of claim 1 wherein the processed cheese has a firmness of at least 10% greater than the firmness of a processed cheese made by the same procedure but without the cross-linking enzyme.

17. The method of claim 1 wherein the processed cheese has a firmness of at least 25% greater than the firmness of a processed cheese made by the same procedure but without the cross-linking enzyme.

18. The method of claim 1 wherein the processed cheese has a firmness of at least 30% greater than the firmness of a processed cheese made by the same procedure but without the cross-linking enzyme.

19. The method of claim 1 wherein at least one other ingredient selected from the group consisting of sorbic acid, sodium chloride, dry cream, concentrated milk fat, whey powder, whey protein concentrate, milk protein concentrate, non-fat dry milk, buttermilk powder and water is used to make the processed cheese.

20. The method of claim 1 wherein the one or more emulsifying agents are selected from the group consisting of trisodium phosphate, sodium citrate, and disodium phosphate.

21. The method of claim 10 wherein the cheese material made from ultrafiltration and diafiltration is allowed to age for a period of at least 24 hours prior to being used to make the processed cheese.

22. The method of claim 10 wherein the cross-linking enzyme is dispersed in water before the cross-linking enzyme and retentate are mixed.

23. The method of claim 10 wherein the retentate is fermented prior to being mixed with the cross-linking enzyme.

24. The method of claim 10 wherein the cross-linking enzyme is mixed with the retentate prior to fermentation, when the retentate has a pH above 5.6, and stays mixed with the retentate as the pH drops below 5.6 during the fermentation.

25. The method of claim 10 wherein the fermented retentate is preheated to a temperature of between about 140° F. and about 212° F. prior to the step of water removal and the cross-linking enzyme is mixed with the fermented retentate after the preheating.

26. The method of claim 2 wherein salt is added to the curds prior to the cheese curds being packed.

27. The method of claim 26 wherein the salt and the cross-linking enzyme are mixed together first and then mixed with the cheese curds.

28. The method of claim 1 wherein both Cheddar cheese and cheese made from ultrafiltration and diafiltration of milk are used to make the processed cheese.

29. The method of claim 28 wherein the cheese material mixed with the cross-linking enzyme comprises the Cheddar cheese.

30. The method of claim 28 wherein the cheese material mixed with the cross-linking enzyme comprises the cheese made from ultrafiltration and diafiltration of milk.

31. The method of claim 28 wherein cross-linking enzyme is mixed with two cheese materials, in that cross-linking enzyme is mixed with cheese curds used to make the Cheddar cheese and with a retentate used to make the cheese made from ultrafiltration and diafiltration of milk.

32. The method of the claim 1 wherein the cheese material contains one or more coagulating agents.

33. The method of claim 32 wherein the one or more coagulating agents comprise a protease.

34. The method of claim 33 wherein the protease comprises rennet.

35. The method of claim 1 wherein the cheese material comprises a pasta filata-type cheese.

36. The method of claim 1 wherein the cheese material comprises an American-type cheese.

37. The method of claim 1 wherein the mixture comprises at least 15% protein during the time that the enzyme is allowed to react.

38. The method of claim 1 wherein the mixture comprises at least 20% protein during the time that the enzyme is allowed to react.

39. The method of claim 1 wherein the mixture comprises at least 10% casein during the time that the enzyme is allowed to react.

* * * * *